United States Patent
Bavouzet et al.

(10) Patent No.: US 11,186,814 B2
(45) Date of Patent: Nov. 30, 2021

(54) YEAST STRAIN HAVING IMPROVED CAPABILITY FOR FERMENTING XYLOSE IN THE PRESENCE OF ACETIC ACID

(71) Applicant: LESAFFRE et COMPAGNIE, Paris (FR)

(72) Inventors: Jean-Michel Bavouzet, Croix (FR); Thomas Desfougeres, Dissay (FR); Georges Pignede, Marcq En Baroeul (FR); Jennifer Techel, Le Bizet (BE)

(73) Assignee: LESAFFRE et COMPAGNIE, Paris (FR)

(*) Notice: Subject to any disclaimer, the term of this patent is extended or adjusted under 35 U.S.C. 154(b) by 0 days.

(21) Appl. No.: 16/793,372

(22) Filed: Feb. 18, 2020

(65) Prior Publication Data

US 2020/0208098 A1 Jul. 2, 2020

Related U.S. Application Data

(62) Division of application No. 15/568,188, filed as application No. PCT/FR2016/050987 on Apr. 27, 2016, now Pat. No. 10,604,735.

(30) Foreign Application Priority Data

Apr. 27, 2015 (FR) ...................................... 1553760

(51) Int. Cl.
| | |
|---|---|
| *C12N 1/14* | (2006.01) |
| *C12N 9/92* | (2006.01) |
| *C12N 7/04* | (2006.01) |
| *C12N 1/18* | (2006.01) |
| *C12N 1/36* | (2006.01) |
| *C12N 1/16* | (2006.01) |
| *C12P 7/10* | (2006.01) |
| *C12P 7/06* | (2006.01) |
| *C12R 1/865* | (2006.01) |

(52) U.S. Cl.
CPC ................. *C12N 1/18* (2013.01); *C12N 1/16* (2013.01); *C12N 1/185* (2021.05); *C12N 1/36* (2013.01); *C12P 7/06* (2013.01); *C12P 7/10* (2013.01); *C12R 2001/865* (2021.05); *Y02E 50/10* (2013.01)

(58) Field of Classification Search
CPC ... C12P 7/02; C12P 9/00; C12N 15/81; C12N 1/16; C12N 9/90; C12Y 503/01005

USPC .......... 435/254.2, 254.21, 99, 145, 157, 161
See application file for complete search history.

(56) References Cited

U.S. PATENT DOCUMENTS

2011/0159560 A1 6/2011 Donaldson et al.

FOREIGN PATENT DOCUMENTS

| WO | WO-2010/000464 A1 | 1/2010 |
|---|---|---|
| WO | WO-2011/080411 A1 | 7/2011 |
| WO | WO-2012/072793 A1 | 6/2012 |
| WO | WO-2013/178915 A1 | 12/2013 |
| WO | WO-2013/178918 A1 | 12/2013 |

OTHER PUBLICATIONS

Bellissimi et al., Effects of acetic acid on the kinetics of xylose fermentation by an engineered, xylose-isomerase-based *Saccharomyces cerevisiae* strain, *FEMS Yeast Research.* 9:358-364 (2009).
International Search Report and Written Opinion of the International Searching Authority, European Patent Office, issued in connection with International Application No. PCT/FR2016/050987, dated Jun. 30, 2016.
Sanda et al., Repeated-batch fermentation of lignocellulosic hydrolysate to ethanol using a hybrid *Saccharomyces cerevisiae* strain metabolically engineered for tolerance to acetic and formic acids, *Bioresource Technology.* 102:7917-7924 (2011).
Wright et al., Batch and continuous culture-based selection strategies for acetic acid tolerance in xylose-fermenting *Saccharomyces cerevisiae*, *FEMS Yeast Research.* 11:299-306 (2011).

*Primary Examiner* — Tekchand Saidha
*Assistant Examiner* — Mohammad Y Meah
(74) *Attorney, Agent, or Firm* — Marshall, Gerstein & Borun LLP

(57) ABSTRACT

The invention relates to a method for selecting a yeast strain having improved capability for fermenting a pentose, advantageously xylose, in the presence of organic acid, advantageously acetic acid, in non-dissociated form, in which at least one yeast strain that is capable of fermenting said pentose is consecutively cultured in the following two media: a first growth medium comprising said pentose as the only carbon source and said organic acid in non-dissociated form; a second growth medium comprising another carbon source as the only carbon source, advantageously glucose, free of said organic acid in non-dissociated form, the consecutive culture in at least said two growth media being repeated at least twice, in the presence of rising concentrations of organic acid in non-dissociated form.

14 Claims, 3 Drawing Sheets

YEAST STRAIN HAVING IMPROVED CAPABILITY FOR FERMENTING XYLOSE IN THE PRESENCE OF ACETIC ACID

CROSS REFERENCE TO RELATED APPLICATIONS

This application is a divisional of U.S. patent application Ser. No. 15/568,188, filed Oct. 20, 2017, which in turn is a U.S. national phase pursuant to 35 U.S.C. § 371 of International Patent Application No. PCT/FR2016/050987, filed Apr. 27, 2016, which claims priority to French Patent Application No. 1553760, filed Apr. 27, 2015, the disclosures of which are all herein incorporated by reference in their entireties.

DOMAIN OF THE INVENTION

The present invention deals with yeast strains able to ferment pentoses, in particular xylose, including in the presence of inhibitors of this fermentation including acetic acid in non-dissociated form.

More specifically, the present invention proposes a method with which to select improved strains that are very effective in their capability to metabolize this type of sugar present in lignocellulose hydrolysates.

DESCRIPTION OF THE PRIOR ART

Lignocellulose or plant biomass, mainly coming from agricultural and agro-industrial activity, is a complex substrate, made of three main fractions which are cellulose, hemicellulose and lignin. It is a matter of potentially recyclable waste, useful for production of ethanol, whose demand is continuing to increase, in light for example of its use as a biofuel.

The method for producing ethanol from lignocellulose biomass consists of recovering as much of the sugars present in the cellulose and hemicellulose fractions as possible by hydrolysis and then transforming them into ethanol by fermentation.

As for the fermentation of the sugars present in this biomass, including both C6 sugars (hexoses) and C5 sugars (pentoses), anaerobic fermentation by yeasts is preferred, in particular using *Saccharomyces cerevisiae*, whose capability for fermenting glucose is well controlled and developed.

However, full attention is given to the fermentation of pentoses, in particular xylose, which can represent up to 25 to 40% of the total sugars contained in the lignocellulose biomass. Thus, yeast strains able to ferment glucose were modified to also be able to metabolize pentoses.

As an example, document WO 2010/000464 reports obtaining yeast strains able to ferment pentoses because of a bacterial gene coding for a xylose isomerase (XI) which converts xylose into xylulose which can be metabolized by the yeast.

As an alternative, a eukaryotic pathway should be noted comprising xylose reductase (XR or XYL1) generating xylitol and a xylitol dehydrogenase (XDH or XYL2) that can also produce xylulose.

Thus, document WO 2012/072793 describes improved yeast strains combining exogenous genes coding a xylose isomerase and a xylitol dehydrogenase with which to eliminate xylitol which proves to be an inhibitor of xylose isomerase. Such strains, in particular the strain deposited at the CNCM (Collection Nationale de Cultures de Microorganismes) on Oct. 5, 2011 under number I-4538, have improved yields and therefore proven industrial utility for the production of ethanol.

Another crucial problem was showing, in the lignocellulose hydrolysates, fermentation inhibitors, among them are furaldehydes (furfural and HMF), phenolic compounds and organic acids (acetic acid, levulinic acid and formic acid). The presence of high concentrations of acetic acid, over 5 g/kg (initial medium) and which can reach 10 g/kg, is intrinsically linked to the concentration of acetyl groups covalently bonded to hemicellulose molecules.

Prior work has taken on the improvement of the resistance of the strains to the presence of acetic acid in the fermentation musts. Thus, document WO 2011/080411 reported obtaining yeast strains whose resistance to acetic acid on glucose was improved.

However, acetic acid is also an inhibitor of xylose fermentation. This inhibition is characterized by a reduction of the xylose consumption kinetics (Bellisimi et al., FEMS Yeast Res., 2009.9:358-364), whereas with glucose, this inhibition is seen as a delay during initiation of fermentation with the kinetics subsequently remaining unchanged. It should be noted that in the presence of both glucose and xylose in the medium, yeast strains ferment glucose first because of catabolite repression.

Thus documents WO 2013/178915 and WO 2013/178918 describe methods for obtaining yeast strains able to metabolize pentoses, in particular xylose, and resistant to fermentation inhibitors, in particular acetic acid.

There is however a clear need to obtain new yeast strains able to ferment hexoses and pentoses with a further reduced impact of fermentation inhibitors, in particular acetic acid, notably on the fermentation kinetics of pentoses such as xylose.

DESCRIPTION OF THE INVENTION

The present invention rests on the inventor showing the possibility of isolating new yeast strains having resistance against fermentation inhibitors, in particular acetic acid, not only involving their glucose metabolism but also involving fermentation of pentoses, including xylose.

In that way and in the context of the invention, a method was developed for selecting yeast strains showing improved fermentation of pentoses, in particular xylose, in the presence of organic acid-type fermentation inhibitors, in particular acetic acid. Using such a method, it was possible to isolate strains having improved xylose fermentation kinetics, in terms of xylose consumption rate, including in the presence of high acetic acid concentrations.

Prior work investigating this problem should be noted:

Thus the document (Wright et al., FEMS Yeast Res., 2011. 11: 299-306) reports the improvement of the resistance of strains against acetate on xylose. This work tends to show that the phenomenon of resistance against acetic acid on xylose could be an inducible process. What is more, the results presented appear to be extremely mixed:

The culture selected by the SBR method ("Single Batch Repeat") or with a xylose-limited chemostat only show a small reduction in the final xylose concentration and consequently a small increase in ethanol concentration during the first three days, compared to the results from the starting strain.

Further, the peak of the specific xylose consumption rate as a function of the acetic acid concentration peaks at a value very close to that observed for the starting strain, 2.5 g/L.

Further, it is observed that with the isolated strain, the specific xylose consumption rate next decreases in a way comparable to what was observed with the starting strain. According to the conclusions drawn, these results would indicate that a prolonged selection in SPR culture cannot lead to a stable phenotype with acetic acid tolerance.

Another document (Sanda et al., Bioresource Technology, 2011. 102:7917-7924) reported implementation of directed evolution on a lignocellulose hydrolysate containing glucose and xylose. However, the SBR techniques which serve to select the fastest multiplying strains lead to the selection of strains growing the fastest on glucose.

Despite failures from the prior art, the inventors developed a new selection method serving to arrive at yeast strains having the desired properties in terms of xylose fermentation in the presence of acetic acid.

According to a first aspect, the present invention relates to a method for selecting a yeast strain having improved capability for fermenting a pentose, in the presence of organic acid, in non-dissociated form.

Thus, the method according to the invention serves to select, from an isolated strain or a mixture of strains, one strain having a selective advantage in terms of growth on a medium containing said pentose and said organic acid in non-dissociated form.

The method, the subject of this application, can be implemented on an isolated strain, in particular on the following strains:

the strain deposited under the Budapest treaty with the CNCM on May 16, 2013 under number I-4749;
the strain deposited under the Budapest treaty with the CNCM on Dec. 12, 2013 under number I-4829;
the strain deposited under the Budapest treaty with the CNCM on Apr. 9, 2015 under number I-4966.

In this scenario and without wanting to be held to any one theory, the selection pressure exerted by the consecutive cultures in the growth media defined below allows the strain to acquire phenotypic traits necessary for increasing its capability for fermenting a pentose in the presence of organic acid in non-dissociated form.

According to another aspect, it is a mixture of yeast strains which undergoes the method according to the invention. In this scenario, at least one of the strains undergoes selection pressure as described above, so as to develop improved capability for fermenting a pentose in the presence of an organic acid in non-dissociated form. Alternatively, the mixture of strains already contains a strain having an improved capability for fermenting a pentose in the presence of organic acid in non-dissociated form and the method according to the invention serves to enrich the mixture in this strain, because of the faster multiplication thereof, and thus isolate or select said strain.

According to a specific embodiment, before their culture in the different growth media according to the invention, the yeast strain or mixture of strains undergoes a prior step of mutagenesis which could enhance the appearance of the desired phenotype. Conventionally, this mutagenesis can be achieved by exposure to a chemical agent or to radiation, in particular ultraviolet (UV) radiation. Advantageously "gentle" conditions are chosen, for example exposure of 100 to 500 $J/cm^2$, for example 300 $J/cm^2$ of UV radiation at 254 nm.

According to the method from the invention, the yeast strain or mixture of strains is cultivated consecutively in at least two growth media. In the context of this application, the expressions "growth medium" and "culture medium" are used indistinguishably for designating a medium comprising the ingredients necessary for the survival and even multiplication of the yeasts that are present.

The first growth medium is characterized in that it comprises, as the only carbon source, the pentose for which improved fermentation capability is sought. It advantageously involves xylose or arabinose, still more advantageously xylose. Advantageously, this first medium is a liquid medium.

Advantageously, the pentose concentration of the growth medium is that commonly implemented when it is used as the only carbon source, specifically included between 5 and 100 g/L in the case of a liquid medium (5 and 100 g/kg in the case of a solid medium), advantageously included between 25 and 90 g/L, for example equal to 50 g/L. According to a specific embodiment, the growth medium contains 50 g/L of xylose.

Said medium also includes the organic acid which could inhibit fermentation of said pentose. It advantageously involves acetic acid or formic acid, still more advantageously acetic acid.

It should be noted that it is known that only the non-dissociated or non-ionized form of such acids have inhibition capability. In the context of the invention, "un-ionized or non-dissociated form" of a carboxylic acid is understood as the protonated form thereof. In practice, the form of such organic acids depends on the pH of the medium in which they are incorporated. At a pH greater than the pKa of the acid, the acid will be mostly found in dissociated form or $COO^-$ ions. In contrast and at a lower pH, the majority form is the non-dissociated or unionized form (COOH). In the remainder of the invention, it will be specified, in particular in connection with the quantities or concentrations, whether only the non-dissociated form of the organic acid present is considered, or whether reference is made to the acetic acid added into the medium, encompassing dissociated and non-dissociated forms depending on the pH of said medium.

Advantageously, the concentration of the organic acid, advantageously as acetic acid, in the non-dissociated form of the growth medium is included between 0.5 and 5 g/L in liquid medium (equivalent to 0.5 and 5 g/kg in solid medium), advantageously between 1.3 and 2.6 g/L. In practice and as an example, this final range corresponds to a concentration of acetic acid added to a growth medium at pH 5 included between 3 and 6 g/L.

According to the invention, this first growth medium is implemented in a growth cycle with at least two or even three media, said cycle being repeated at least twice. In a way adapted to the invention, during at least two growth cycles, the concentration of organic acid in non-dissociated form is increased.

In other words, the consecutive culture in at least two growth media defined in connection with the invention is repeated twice, in the presence of rising concentrations of organic acid, advantageously of acetic acid, in non-dissociated form. Thus and in the presence of n cycles (with n greater than or equal to 2), at least two concentrations are implemented, with the first concentration lower than the second concentration.

As an example and for 8 cycles of culture in the presence of acetic acid, a plan for increasing the concentration in the first growth medium can be the following:

$1^{st}$ cycle: acetic acid concentration added to a medium at pH 5 equal to 3 g/L (or 1.3 g/L of acetic acid in dissociated form);

$2^{nd}$ cycle: acetic acid concentration added to a medium at pH 5 equal to 3 g/L (or 1.3 g/L of acetic acid in non-dissociated form);

3$^{rd}$ cycle: acetic acid concentration added to a medium at pH 5 equal to 3 g/L (or 1.3 g/L of acetic acid in non-dissociated form);

4$^{th}$ cycle: acetic acid concentration added to a medium at pH 5 equal to 4 g/L (or 1.7 g/L of acetic acid in non-dissociated form);

5$^{th}$ cycle: acetic acid concentration added to a medium at pH 5 equal to 4 g/L (or 1.7 g/L of acetic acid in non-dissociated form);

6$^{th}$ cycle: acetic acid concentration added to a medium at pH 5 equal to 4 g/L (or 1.7 g/L of acetic acid in non-dissociated form);

7$^{th}$ cycle: acetic acid concentration added to a medium at pH 5 equal to 5 g/L (or 2.15 g/L of acetic acid in non-dissociated form);

8$^{th}$ cycle: acetic acid concentration added to a medium at pH 5 equal to 6 g/L (or 2.6 g/L of acetic acid in non-dissociated form).

Beyond these two ingredients, this growth medium is advantageously a complete synthetic medium, suited to the growth of yeast and can contain conventional ingredients such as salts, buffers, yeast extract or any other source of nitrogen the yeast can metabolize, vitamins, etc. In the context of the invention, "synthetic medium" is understood to be a medium whose chemical composition is known.

According to a specific embodiment, other than pentose as the only carbon source and the organic acid, such a medium can include:

Yeast extract, advantageously at a concentration of 5 g/L;
Diammonium phosphate, advantageously at a concentration of 4.7 g/L;
Citric acid, advantageously at a concentration of 11.4 g/L;
Trisodium citrate, advantageously at a concentration of 13.5 g/L;
$ZnSO_4$, advantageously at a concentration of 21.2 mg/L;
$MgSO_4$ $7H_2O$, advantageously at a concentration of 1 g/L;
Thiamine, advantageously at a concentration of 18.24 mg/L;
Pyridoxine, advantageously at a concentration of 5.28 mg/L;
Biotin, advantageously at a concentration of 1.76 g/L;
Pantothenate, advantageously at a concentration of 3.8 mg/L;
Niacin, advantageously at a concentration of 20 mg/L;
Meso-inositol, advantageously at a concentration of 50 mg/L;
Riboflavin, advantageously at a concentration of 1 mg/L;
Para-aminobenzoate, advantageously at a concentration of 1.2 mg/L;
Tween 80, advantageously at a concentration of 1 g/L.

Beyond the specific composition of this growth medium, the culture for the yeast strain or mixture of strains is advantageously made under standard conditions favorable to the growth of yeasts, in particular *Saccharomyces* type, and their fermentation activity, specifically:

An acid pH advantageously included between 4 and 6, even 4.5 and 5.5, even more advantageously equal to 5;
A temperature included between 28 and 37° C., even between 30 and 35° C., advantageously equal to 32° C.;
Under gentle stirring, for example equal to 100 rpm;
Under reduced conditions of oxygen supply (under limited $O_2$). In practice, the culture can be made in a flask stoppered using a cap reducing the supply of $O_2$ in the medium while allowing evacuation of the $CO_2$ produced.

Generally, the culture is stopped when the source of hydrolyzable glucidic carbon, in this case the pentose, has been completely consumed. In practice, and advantageously, the culture is left for at least 24 hours, even several days, advantageously for seven days.

The second step of the method according to the invention consists of transferring the yeasts cultivated in the first growth medium into a second growth medium, which is advantageously liquid. Characteristically, this is distinguished from the first culture medium by the presence of a different carbon source and by the absence of organic acid, advantageously of acetic acid, in non-dissociated form.

In practice, this medium is favorable to the growth of yeasts and allows lifting adaptation phenomena to the benefit of the acquisition of stable mutations. Thus, this step of the method according to the invention is considered as a de-adaptation phase.

This growth medium is characterized in that it comprises, as only carbon source, a carbon source different from that of the first culture medium, specifically a pentose, in particular a xylose. According to a specific embodiment, the carbon source from the second culture medium is a source of hydrolyzable glucidic carbon, advantageously a hexose, still more advantageously glucose. Advantageously, the concentration of this second carbon source, advantageously glucose, is included between 5 and 50 g/L, advantageously included between 5 and 20 g/L, for example equal to 20 g/L.

Further and advantageously, it involves a rich synthetic growth medium, comprising for example:

yeast extract, advantageously at a concentration of 10 g/L;
peptone, advantageously at a concentration of 10 g/L.

Advantageously, it is therefore a matter of a rich medium allowing all strains of yeast to multiply without any limitation which would be linked to any auxotrophy.

Beyond the specific composition of this second growth medium, the culture for the yeast strain or mixture of strains is advantageously made under standard conditions favorable to the growth of the yeast, specifically:

An acidic and stable pH, advantageously included between 4 and 6, for example equal to 5;
A temperature included between 28 and 37° C., even between 30 and 35° C., advantageously equal to 30° C.;
Under medium stirring, for example equal to 150 rpm;
In the presence of oxygen, specifically aerobiosis. In practice, the culture can be made in a baffled flask stoppered by a porous cap which allows the supply of $O_2$ in the medium while allowing evacuation of the $CO_2$ produced.

There again, the culture is stopped when the source of hydrolyzable glucidic carbon, advantageously glucose, has been completely consumed. It should be noted that in practice the growth in the second medium is faster than in the first medium because of the aerobiosis, the glucose as carbon source and the absence of acetic acid. Thus and advantageously, the culture is done over several hours, advantageously 24 hours.

According to the invention, the culture of the yeasts consecutively in the two growth media and under the conditions described above constitutes one cycle.

According to a specific embodiment, a cycle in the method according to the invention further comprises the passage of the yeast into a third growth medium, advantageously liquid, intended to select the cells capable of respiration, specifically having functional mitochondria. In practice, this step, which can be implemented with each cycle or at least once in the method, serves to overcome the appearance of "petites" whose respiratory-deficient phenotype can be disadvantageous in the context of industrial yeast production methods.

Advantageously, this third medium is a poor or minimum medium containing as the only carbon source a carbon which can only be used by cells which retained functional mitochondria. In this case, one is speaking of a source of strict respiratory carbon, meaning a carbon source systematically involving mitochondrial oxidation and not producing ethanol. It can advantageously be glycerol or possibly ethanol. In other words such a medium is free of fermentable sugar. Advantageously, the glycerol concentration of the growth medium is that commonly used when it is used as the only carbon source, specifically included between 5 and 50 g/L, advantageously included between 10 and 50 g/L, for example equal to 10 g/L so as to obtain sufficient biomass for inoculating the first culture medium of the following cycle.

By definition, a minimum medium contains, other than a carbon source, a nitrogen source, a potassium source, a phosphorous source, a sulfur source, a magnesium source, a calcium source, an iron source, a source of trace elements and of water.

A medium which can be used for preparation of this third culture medium may include:
  a base, such as DIFCO® yeast nitrogen base, advantageously at a concentration of 3.4 g/L;
  and optionally ammonium sulfate, advantageously at a concentration of 5 g/L.

Beyond the specific composition of this third growth medium, the culture for the yeast strain or mixture of strains is advantageously made under standard conditions favorable to the growth of yeasts, specifically:
  An acid pH advantageously included between 4 and 6, even 4.5 and 5.5, for example equal to 5;
  A temperature included between 28 and 37° C., even between 30 and 35° C., advantageously equal to 30° C.;
  Under medium stirring, for example equal to 150 rpm;
  In aerobiosis. In practice, the culture can be made in a baffled flask stoppered by a porous cap which allows the supply of $O_2$ in the medium.

There again, the culture is stopped when the carbon source, advantageously glycerol, has been completely consumed. It should be noted that in practice the growth in this medium is a priori less quick than in the second medium because of the mineral source of nitrogen. Thus and advantageously, the culture is done over several hours, advantageously 48 hours.

As already mentioned, the method according to the invention is characterized in that the culture of the yeast strain, consecutively in the two or three growth media described above, is iterated in the form of cycles.

The number of cycles is chosen so as to enhance the selection of the strain having the desired characteristics, specifically an improved capability for fermenting a pentose in the presence of an organic acid inhibitor, while also limiting the number of cycles for avoiding the appearance of unsoundnesses in the yeast.

Thus and advantageously, the number of cycles is at least equal to two and advantageously less than or equal to 10, for example equal to 8. In other words, the consecutive culture in the at least two growth media as defined is repeated at least two times, advantageously more than 2 times but less than 10 times, for example 8 times.

According to an advantageous embodiment of the method according to the invention, the consecutive culture in at least the two growth media is repeated at least twice, in the presence of rising concentrations of organic acid, advantageously acetic acid, in non-dissociated form. In other words, the method according to the invention is done in the presence of at least two distinct concentrations with the first concentration less than the second. This concentration can be increased gradually, possibly by thresholds. Thus and advantageously for the adaptation of the yeast strains, at least the first two cycles are done at constant concentration.

According to another advantageous aspect, the concentration of organic acid, advantageously acetic acid, in non-dissociated form in the first growth medium is included between 1.3 and 2.6 g/L.

When the desired number of cycles is reached and for obtaining differentiated clones, the culture is advantageously spread on a solid medium, still more advantageously on a synthetic medium favorable to the growth of yeasts, such as the YPG medium. The seeding level is typically 2000 cells per plate and the growth takes place at 30° C. for about 72 hours.

In a specific embodiment, the performance of the clones isolated this way is tested.

For this purpose, pre-cultures in liquid medium, advantageously in a synthetic medium suitable to the growth of yeast, such as the YPG medium, can be prepared.

Advantageously, these pre-cultures allow the seeding of the selection medium, specifically a medium equivalent to the first growth medium described above, comprising as the only carbon source said pentose, advantageously xylose, and said organic acid, advantageously acetic acid, in non-dissociated form. Preferably, an average acetic acid concentration is chosen, for example equal to 5 g/L for a medium with pH 5.

Advantageously the selected clones are the ones having the best growth in this medium. The growth level can be determined by the analysis of the turbidity using an optical density measurement from a spectrophotometer at a wavelength included between 600 and 700 nm, for example equal to 630 nm. In practice, the growth can be evaluated in DeepWell type microplates or a liquid medium under the conditions stated below, specifically:
  An acid pH advantageously included between 4 and 6, even 4.5 and 5.5, even more advantageously equal to 5;
  A temperature included between 28 and 37° C., even between 30 and 35° C., advantageously equal to 32° C.;
  Under gentle stirring, for example equal to 100 rpm, or without stirring;
  Under reduced conditions of oxygen supply (under limited $O_2$ or anaerobiosis);
  A growth time of at least 24 hours, for example 72 hours.

The seeding rate must therefore be moderate to prevent a "titrating" effect of the yeast, for example equal to 0.25 g/kg equivalent DM (DM=dry material).

An important first criterion is therefore the capability of the one or more selected yeast strains to grow in a medium containing a pentose, in particular xylose, in the presence of an organic acid type inhibitor, in particular acetic acid, in non-dissociated form.

According to another embodiment, the selection method can comprise a step for evaluation of the mass loss as a function of fermentation time in the selection medium and under conditions as defined above. The measurement of the mass loss from the fermentation flask is correlated with the production of alcohol. Tracking this mass loss therefore reflects the kinetics of pentose, advantageously xylose, fermentation in the presence of an organic acid-type inhibitor, in particular acetic acid, and non-dissociated form.

Under these conditions and in the presence of only pentose as carbon source (no glucose), the expected profile is single phase, with an associated ax+b type kinetics when the sugar is in a nonlimiting concentration (at the start of the culture). In the context of the selection of an advantageous strain, in particular for its pentose, in particular xylose, fermentation rate, the value a (positive number) is as high as possible.

Further, a strain of yeast is sought capable of resisting acetic acid in xylose medium, and doing so including at high acetic acid concentrations. Thus, the maximum $CO_2$ production rate can be measured during xylose fermentation on a medium as previously described but containing variable concentrations of acetic acid from the fermentation medium.

For a given acetic acid concentration, it is preferred that the selected strain have a maximum xylose consumption speed, equal to twice the mass loss by fermentation, greater than already isolated strains, and do so whatever the acetic acid concentration (including in the absence of acetic acid), advantageously in the concentration range of real media, for example between 4 and 8 g/kg.

Further and according to an advantageous embodiment, it is verified that the capability of the selected strain to ferment glucose (hexose) and xylose (pentose) in the presence of the organic acid, advantageously acetic acid, in non-dissociated form is not affected. It is therefore then a matter of analyzing the fermentation characteristics in general, in a medium near real media containing both hexoses and pentoses.

In practice the fermentation is done on a YFP type rich medium, containing glucose, xylose and acetic acid, for example a medium comprising:

Yeast extract, advantageously at a concentration of 10 g/L;
Bacto-peptone, advantageously at a concentration of 10 g/L;
Glucose, advantageously at a concentration of 55 g/L;
Xylose, advantageously at a concentration of 45 g/L;
Acetic acid, advantageously with a quantity added to the medium at a concentration of 5 g/L;
KOH.

The culture conditions are those suited to the growth and fermentation of yeast, advantageously:

An acid pH advantageously included between 4 and 6, even more advantageously equal to 5;
A temperature included between 28 and 37° C., even between 30 and 35° C., advantageously equal to 32° C.;
Under gentle stirring, for example equal to 100 rpm;
Under reduced conditions of oxygen supply (under limited $O_2$ or anaerobiosis);
A growth time of at least 24 hours, for example 72 hours.

The seeding rate must therefore be moderate to prevent a "titrating" effect of the yeast, for example equal to 0.25 g/kg equivalent DM (DM=dry material).

A profile is expected which shows the double effect of the acetic acid on the yeasts able to ferment xylose and glucose:

During the first phase, called the "glucose phase", a delayed initiation of the fermentation which is a short as possible, advantageously under 24 hours, still more advantageously of order 5 to 6 hours. Preferably, the selected strain has therefore not lost resistance to acetic acid during glucose fermentation.
During xylose fermentation, kinetics as favorable as possible, meaning as fast and high as possible, with better performance than the strains from the prior art.

According to an advantageous embodiment, the method according to the invention is implemented on the strain of yeast having attractive properties in connection with the targeted application:

Good growth in synthetic and natural media;
Capability for fermenting glucose including, advantageously, in the presence of an organic acid, in particular acetic acid, in non-dissociated form;
Capability for fermenting xylose including, advantageously, in the presence of an organic acid, in particular acetic acid, in non-dissociated form;
And, advantageously, reduced inhibition of the glucose fermentation pathway by acetic acid.

Such strains are for example chosen from the following group:

the strain deposited under the Budapest treaty with the CNCM on Oct. 5, 2011 under number I-4538;
the strain deposited under the Budapest treaty with the CNCM on May 16, 2013 under number I-4749;
the strain deposited under the Budapest treaty with the CNCM on Dec. 12, 2013 under number I-4829;
the strain deposited under the Budapest treaty with the CNCM on Apr. 9, 2015 under number I-4966.

Preferred strains are the strain deposited with the CNCM on Dec. 12, 2013 under number I-4829 and/or the strain deposited with the CNCM on Apr. 9, 2015 under number I-4966.

Preferably, the strains selected at the end of the method according to the invention retain the characteristics of interest from the strains used for implementing said method.

According to another aspect, the present invention relates to a yeast strain obtained using the method described above.

Remarkably, such a strain has a capability for fermenting xylose in the presence of acetic acid that is still unequaled.

This capability is advantageously measured under the following conditions:

A pre-culture of the strain is made in liquid medium, advantageously a synthetic medium favorable to the growth of yeast, such as the YPG medium, and under conditions described in connection with the second medium used in the method described above.

After 24 to 72 hours of culture at 30° C., the strain is transferred into a growth medium such as the first growth medium of the method according to the invention. Such a medium is advantageously defined as follows:

Yeast extract, advantageously at a concentration of 5 g/L;
Diammonium phosphate, advantageously at a concentration of 4.7 g/L;
Citric acid, advantageously at a concentration of 11.4 g/L;
Trisodium citrate, advantageously at a concentration of 13.5 g/L;
$ZnSO_4$, advantageously at a concentration of 21.2 mg/L;
$MgSO_4$ $7H_2O$, advantageously at a concentration of 1 g/L;
Thiamine, advantageously at a concentration of 18.24 mg/L;
Pyridoxine, advantageously at a concentration of 5.28 mg/L;
Biotin, advantageously at a concentration of 1.76 g/L;
Pantothenate, advantageously at a concentration of 3.8 mg/L;
Niacin, advantageously at a concentration of 20 mg/L;
Meso-inositol, advantageously at a concentration of 50 mg/L;
Riboflavin, advantageously at a concentration of 1 mg/L;
Para-aminobenzoate, advantageously at a concentration of 1.2 mg/L;
Tween 80, advantageously at a concentration of 1 g/L.

It additionally contains xylose as an only carbon source, at a concentration advantageously equal to 50 g/L and variable concentrations of acetic acid ranging preferably from 0 to 10 g/L so as to be able to establish a dose-response curve. Here it involves values for quantities of acetic acid added to the culture medium at pH 5.

The conditions for seeding and culture are advantageously the following:
- An acid pH advantageously included between 4 and 6, even 4.5 and 5.5, even more advantageously equal to 5;
- A temperature included between 28 and 37° C., even between 30 and 35° C., advantageously equal to 32° C.;
- Under gentle stirring, for example equal to 100 rpm;
- Under reduced conditions of oxygen supply (under limited $O_2$ or anaerobiosis);
- A growth time of at least 24 hours, advantageously 72 hours;
- A seeding rate advantageously equal to 0.25 g/kg equivalent DM (DM=dry material).

At the end of this culture, the maximum $CO_2$ production rate is determined for each acetic acid concentration.

Under these conditions, the selection of yeast strains having the following characteristics never obtained by strains from the prior art was reported for the first time: The acetic acid dose needed to reduce xylose consumption kinetics 50% is greater than 2.5 g/L in liquid medium (2.5 g/kg in solid medium), even 3 g/L, even greater than or equal to 3.5 g/L, advantageously greater than 4 g/L, or even greater than or equal to 5 g/L. Here it involves values for quantities of acetic acid added to the culture medium at pH 5.

In practice, faster xylose fermentation kinetics in real media, typically comprising from 2 and 8 g/kg of acetic acid, results. Thus and in the presence of a strain according to the invention, it is possible to conceive of total fermentation of the sugars present in under 72 hours, advantageously between 48 and 72 hours.

According to a particular embodiment, the yeast strain targeted by the invention comprises at least one copy of an exogenous gene coding for xylose isomerase, advantageously from *Clostridium phytofermentans*. In connection with the invention, "exogenous" is understood to mean the fact that the gene comes from another organism.

According to another specific embodiment, the yeast strain targeted by the invention comprises at least one supernumerary copy of the GAL2 gene coding for a hexose transporter also capable of capturing xylose. According to another embodiment, said strain comprises at least two supernumerary copies of the GAL2 gene. This can be placed under the control of a pADH1-type strong, constitutive promoter.

According to other specific embodiments, the yeast strain targeted by the invention has one or more characteristics chosen from the following group:
- suppression of aldose reductase activity (GRE3);
- overproduction of xylulokinase (XKS1), in particular by modification of the promoter or introduction of supernumerary copies;
- expression or overproduction of the pentose phosphate pathway (RPE1, RKL1, TKL1, TAL1, etc.);
- absence of xylose reductase (XR) activity;
- the capability for fermenting arabinose, advantageously because of the insertion of a bacterial pathway such as described in WO 2008/041840 or European patent 1,499,708.

According to an advantageous embodiment, the yeast strain targeted by the present invention belongs to the Hemiascomycetes group. Preferred strains belong to the *Saccharomyces*, *Candida*, *Pichia* and *Yarrowia* genera, advantageously *Saccharomyces*. Among *Saccharomyces*, it advantageously involves *Saccharomyces cerevisiae*.

As shown in the context of the present application, a strain conforming to the invention is the strain deposited under the Budapest treaty at the CNCM (Collection Nationale de Cultures de Microorganismes, Institut Pasteur, 25 rue du Docteur Roux, 75724 Paris Cedex 15) under number I-4953 on Jan. 29, 2015.

In the context of the invention, "yeast strain" is understood to be a genetically rigorously identical population of yeast. This encompasses both strains referred to as laboratory strains and those referred to as industrial strains.

According to another aspect, the present invention also targets a yeast obtained by culture of a strain as defined above.

In the context of the invention, "yeast" is understood as a commercial product obtained by implementation of a production method for a yeast strain. Thus, yeasts having different properties can be obtained from a single strain, where these differences are connected with the production method implemented.

According to another aspect, the invention relates to the use of a strain or yeast as defined above for the fermentation of a material, advantageously containing xylose and/or glucose, and/or for ethanol production. According to a specific embodiment, the material is a lignocellulose material. Such material typically contains:
- Pentoses, in particular D-xylose and L-arabinose;
- Hexoses, in particular D-mannose, D-galactose, L-rhamnose and D-glucose;
- Uronic acids.

According to a specific aspect, the invention deals with a production method for fermentation products or ethanol comprising the following steps:
- Incubation of a material or medium containing xylose with a strain or a yeast as defined above;
- Fermentation under anaerobic or semi-anaerobic conditions;
- Recovery of the one or more fermentation products, or ethanol.

According to a specific embodiment of this method, the material or medium also contains glucose.

The present invention is going to be illustrated more ahead using the following example embodiments, supported by the attached figures. However, they have no limiting scope.

LEGENDS FOR THE FIGURES

EXAMPLE EMBODIMENTS

Figure 1:
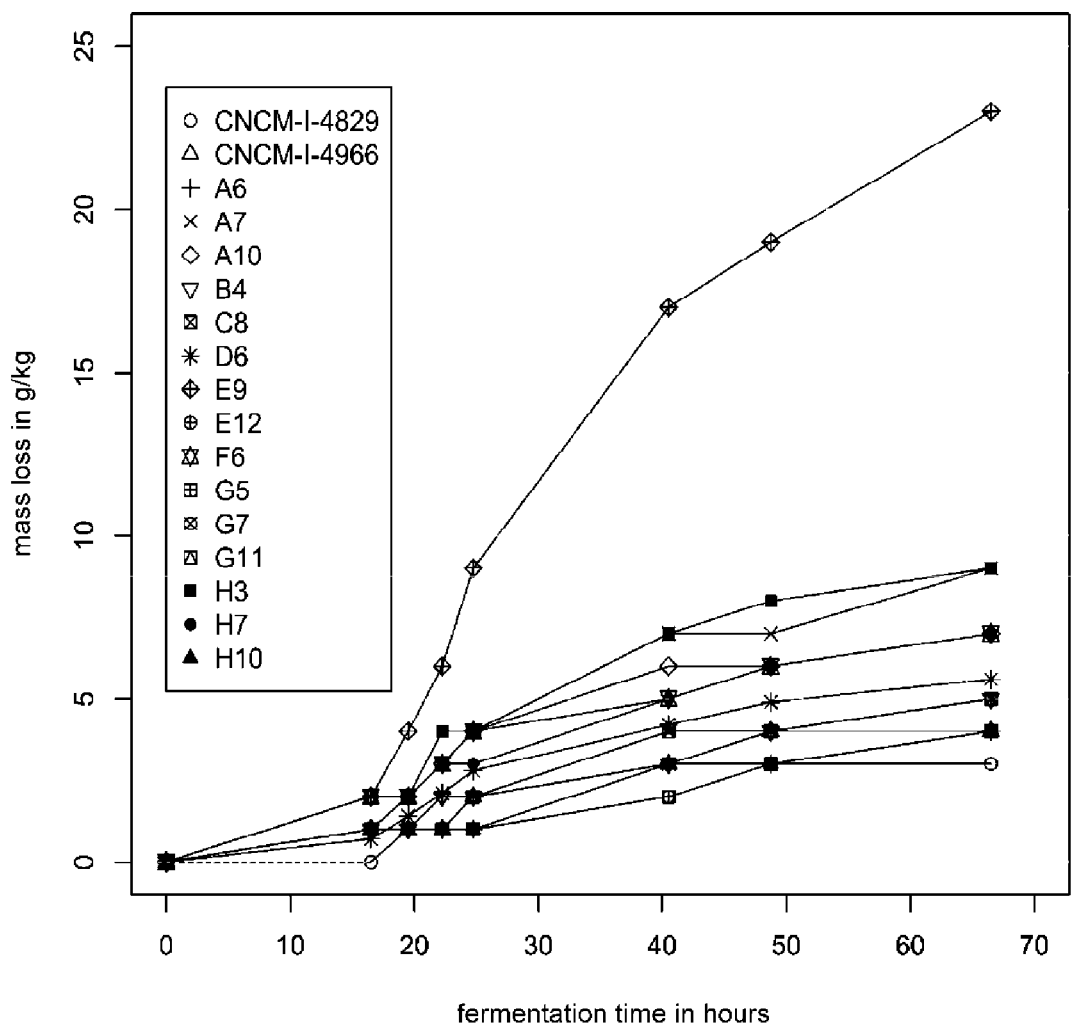
FIG. 1 shows the progression of the mass loss (expressed in g/kg) as a function of fermentation time for various strains, in a medium containing 50 g/L xylose and 5 g/L acetic acid at pH=5.

I) Material and Methods:
1) Strain:
Yeast: *Saccharomyces cerevisiae*
Strain: I-4829 or I-4966

2) Culture Medium and Conditions:
2-a) Directed Evolution:
Medium 1: YFX50=
  Xylose 50 g/L;
  Yeast extract 5 g/L;
  Di-ammonium phosphate 4.7 g/L;
  Citric acid 11.4 g/L;
  Trisodium citrate 13.5 g/L;
  $ZnSO_4$ 21.2 mg/L;
  $MgSO_4$ $7H_2O$ 1 g/L;
  Thiamine 18.24 mg/L;
  Pyridoxine 5.28 mg/L;
  Biotin 1.76 g/L;
  Pantothenate 3.8 mg/L;
  Niacin 20 mg/L;
  Meso-inositol 50 mg/L;
  Riboflavin 1 mg/L;
  Para-aminobenzoate 1.2 mg/L;
  Tween 80, 1 g/L.

The yeasts are cultivated in this medium with xylose as the only carbon source and with acetic acid whose concentration increases over the cycles (see Results section).

The pH of the medium is kept at 5.

The culture is done at 32° C. with stirring at 100 rpm in flasks stoppered by caps which serve to reduce the supply of oxygen in the medium and allow $CO_2$ which is produced throughout this culture in excess pressure to escape. Under these conditions, the culture lasts about seven days.

Medium 2 (YPG):
  10 g/L of yeast extract;
  10 g/L de peptone;
  20 g/L of glucose as the only carbon source.

The culture is done at 30° C. with stirring at 150 rpm in baffled flasks stoppered by porous caps which allow the supply of oxygen into the medium. Under these conditions, the culture lasts 24 hours.

Medium 3:
  3.4 g/L of DIFCO® yeast nitrogen base;
  5 g/L of ammonium sulfate;
  10 g/L of glycerol as the only carbon source.

The culture is done at 30° C. with stirring at 150 rpm in baffled flasks stoppered by porous caps which allow the supply of oxygen into the medium. Under these conditions, the culture lasts 24 to 48 hours.

2-b) Selection of the Most Effective Strains:

At the end of the eighth cycle, the cells were spread at a concentration of 2000 cells per dish (150 mm diameter) of agar medium (YPG+agar).

The resulting colonies were then cultivated in Deep Well format (=96–well microplate) in a YPG medium.

After 72 hours of culture at 30° C., the colonies were transferred into a YFX50-Ac-5000 medium whose composition is indicated below:

| YFX50-Ac-5000 | g/kg | mL/kg |
|---|---|---|
| Distilled water qs | 1000 | |
| Xylose | 50 | |
| Yeast extract type J | 5 | |
| DAP | 4.7 | |
| Citric acid | 11.4 | |
| Trisodium citrate | 13.5 | |
| Acetic acid | 5 | |
| pH 5 | | |
| $ZnSO_4$ (10.6 g/L) | | 2 |
| $MgSO_4$ $7H_2O$ (400 g/L) | | 2.5 |
| Distilled water qs | 1000 | |
| Xylose | 50 | |
| Yeast extract type J | 5 | |
| DAP | 4.7 | |
| Citric acid | 11.4 | |
| Trisodium citrate | 13.5 | |
| Acetic acid | 5 | |
| Thiamine Vit B1 (18.24 g/L) | | 1 |
| Pyrodixine Vit B6 (5.28 g/L) | | 1 |
| Biotin (1.76 g/L) + KOH | | 1 |
| Pantothenate (3.8 g/L) | | 1 |
| Nicotinic acid (8 g/L) | | 2.5 |
| Meso-inositol (50 g/L) | | 1 |
| Riboflavin (1 g/L) | | 1 |
| Para-aminobenzoate (1.2 g/L) | | 1 |
| Tween 80 | | 1 |

In practice, it involves the same culture medium as the first growth medium used in the method according to the invention, with an acetic acid concentration (quantity added into the culture medium at pH 5) equal to 5 g/L.

Likewise, the culture conditions are similar:

Conditions:
  pH: 5
  Temperature: 32° C.
  $O_2$ conditions: without oxygen supply (anaerobic)
  Stirring: 100 rpm
  Length of the culture: 72 hours Pre-Culture/Incubation:
  Take up the colonies for the liquid cultures from Deep Well (96-well micro plates);
  0.25 g/kg equivalent DM for liquid cultures.

2-c) Validation of the Isolated Strains
  Medium: YFP-5000
    10 g/L of yeast extract;
    10 g/L of bacto-peptone;
    55 g/L of glucose;
    45 g/L de xylose;
    5 g/L of acetic acid (quantity added to the culture medium at pH 5);
    KOH.

Conditions:
  pH: 5
  Temperature: 32° C.
  $O_2$ conditions: without oxygen supply
  Stirring: 100 rpm
  Length of the culture: up to 72 hours
  Pre-Culture/Incubation: 0.25 g/kg eq DM of yeast previously propagated in YPG medium.

3) Evaluation of the Mass Loss:

The ethanol production is measured indirectly by a measurement of the mass lost from the fermentation flask, since this mass loss is directly correlated with alcohol production. It is expressed in grams per kilogram of medium.

4) Evaluation of the $CO_2$ Production Speed:

Starting with the determination of the mass loss (corresponding to $CO_2$ production), it is possible to determine the xylose consumption rate (expressed in g/L) which is twice the mass loss.

The maximum $CO_2$ production rate is expressed in $g \cdot kg^{-1} \cdot h^{-1} \cdot g^{-1}$ of DM (dry material).

II) Results:

1) Selection of Strains of Interest:

1-a) Directed Evolution:

The directed evolution was done in Single Batch Repeat mode:

Cycles 1 to 3: medium 1 with 3 g/L of acetic acid (added into the medium at pH 5) and then medium 2 and then medium 3;

Cycles 4 to 6: medium 1 with 4 g/L of acetic acid and then medium 2 and then medium 3;

Cycle 7: medium 1 with 5 g/L of acetic acid and then medium 2 and then medium 3;

Cycle 8: medium 1 with 6 g/L of acetic acid and then medium 2 and then medium 3;

1-b) Selection of the Most Effective Strains:

After isolation of the clones on solid medium and their pre-culture in liquid medium, they are seeded in the Deep Well type micro plates containing the medium YFX50-Ac-5000 (50 g/kL of xylose and 5 g/L of acetic acid at pH=5).

After 72 hours of fermentation in this medium, the selected strains (16 in total) are those having the best growth, by analysis of the cellular density of the medium. Strains CNCM I-4071 and CNCM I-4829 served respectively as negative and positive control for the capability of the cells to use xylose for their growth.

These 16 strains were evaluated on the kinetics on this same medium. The results are shown in FIG. 1 which shows the mass loss as a function of the fermentation time. As expected, since this medium contained only xylose (no glucose), the observed profile for all strains tested is single phase. On the other hand, it appears that the derivative at the beginning of the curve varies depending on the strains. This can be formulated using the equation ax+b, where a varies according to the strains.

FIG. 1 shows that strain E9 shows the best performance. The strain was deposited with Institut Pasteur (Collection Nationale de Cultures de Microorganismes, 25 rue du Docteur Roux, 75724 Paris Cedex 15) under number CNCM I-4953 on Jan. 29, 2015 and was used in the remainder the experiments.

2) Properties of Strain 1-4953:

2-1) in Xylose Medium:

The first step consisted of determining the impact of the directed evolution on the capability of this strain to resist acetic acid during xylose fermentation. To do that, the test consisted of measuring the maximum $CO_2$ production rate during the xylose fermentation on a YFX50-Ac medium. In order to obtain a dose-response curve, various acetic acid concentrations were added to the fermentation medium.

Figure 2:
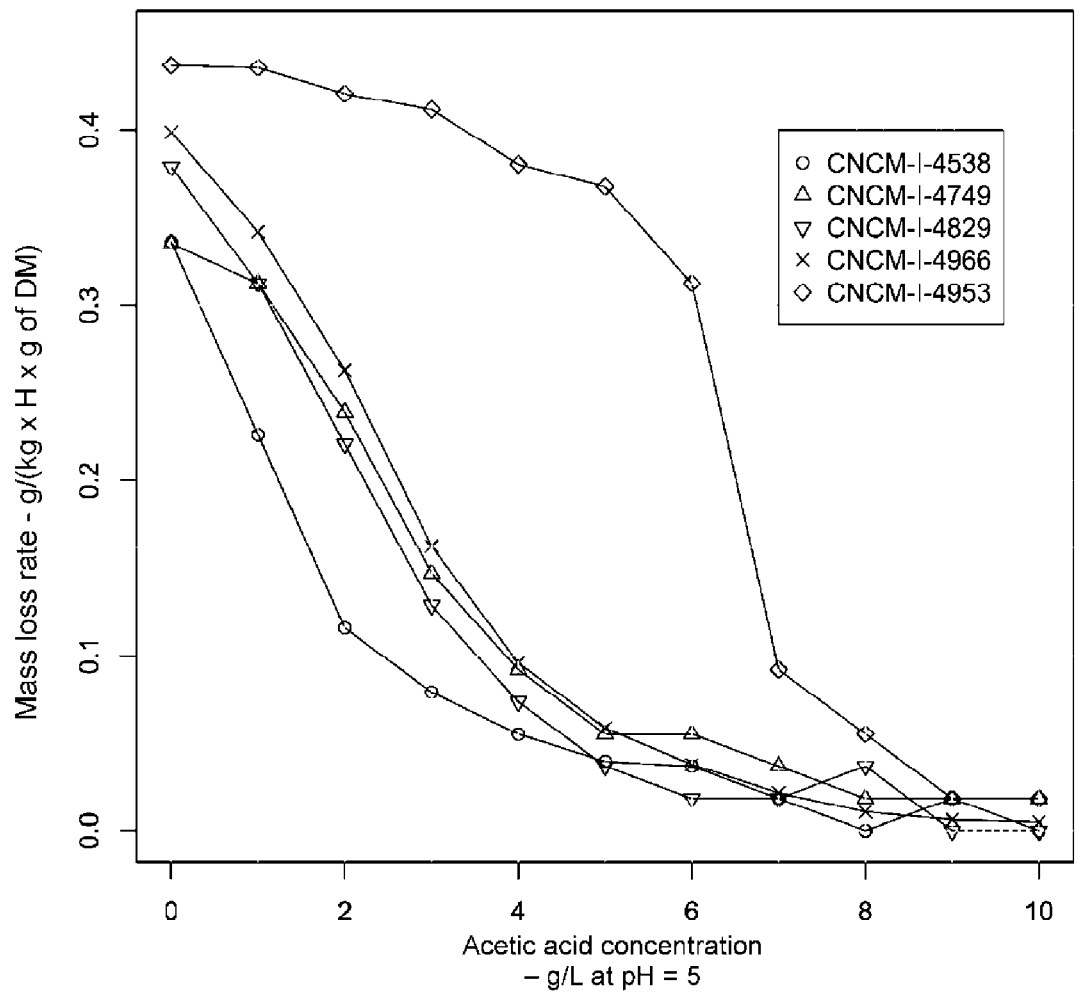
FIG. 2 shows the impact of acetic acid concentration (expressed in g/L at pH 5) on the mass loss rate (production of $CO_2$ from xylose), during fermentation of various strains, in a medium containing 50 g/L xylose.

FIG. 2 shows that this strain has a maximum xylose consumption rate equal to twice the mass loss during fermentation which is about 15% greater than the rate for the strain I-4829 without acetic acid. This gap is even greater when the acetic acid dose is 4 g/L. In fact, at this concentration, the xylose consumption rate is reduced by 85% for strain I-4829, compared to only 15% for strain I-4953. This means that in the presence of 4 g/L acetic acid and at pH 5, strain I-4953 has the same xylose consumption rate as strain I-4829 without acetic acid.

2-2) in Glucose+Xylose Medium:

In order to better understand the impact of the directed evolution on the fermentation in general, the mass loss as a function of fermentation time was tracked for a medium containing glucose, xylose and acetic acid.

Figure 3:
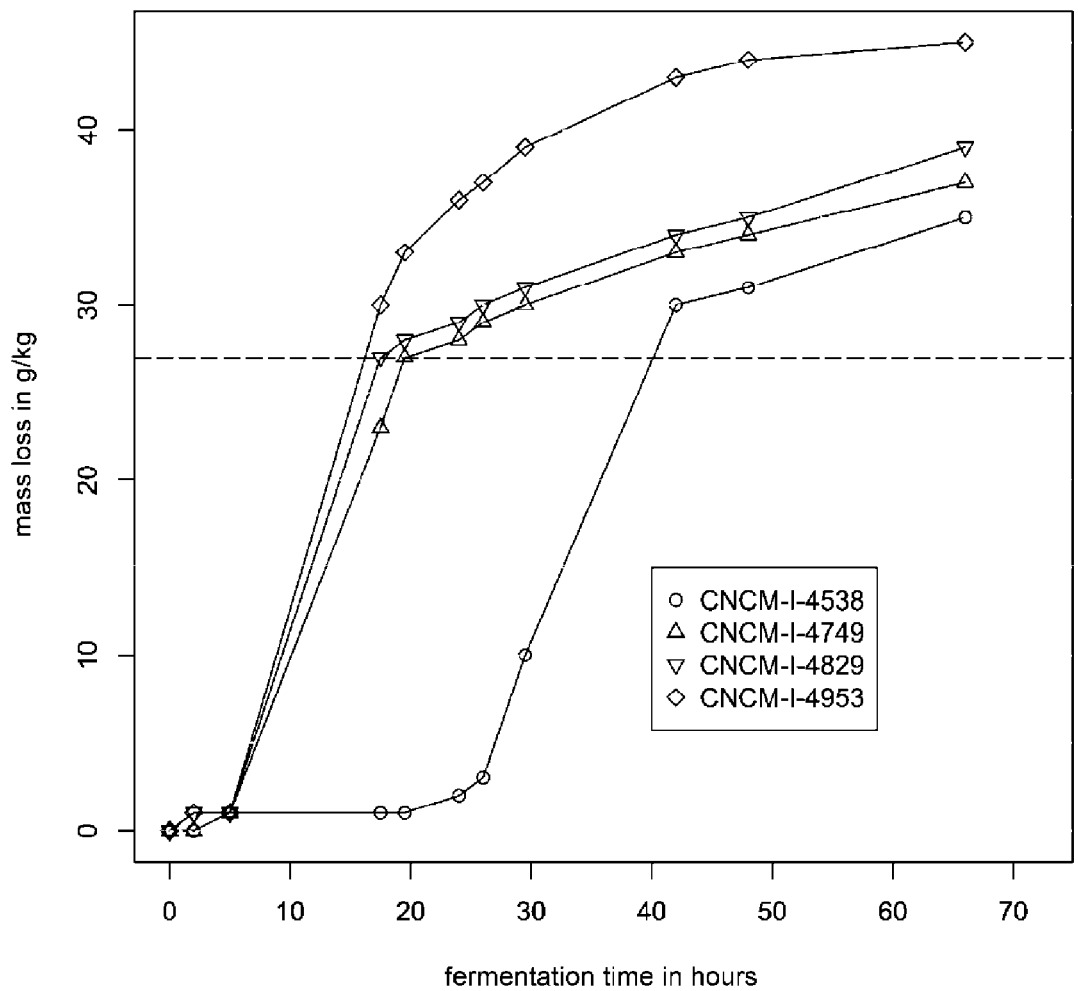
FIG. 3 shows the progression of the mass loss (expressed in g/kg) as a function of fermentation time for various strains, in a medium containing 55 g/L glucose, 45 g/L xylose and 5 g/L acetic acid (at pH 5).

The results are shown in FIG. 3 which clearly shows the double effect of acetic acid on yeasts capable of fermenting xylose:

During the first phase, called the "glucose phase", strain 1-4538 shows a fermentation initiation delay of about 24 hours. For the other strains (I-4749, I-4829 and I-4953), the lag is only 5 to 6 hours. This observation means that the isolated strain has not lost resistance to acetic acid during glucose fermentation.

When xylose fermentation picks up the relay, the kinetics of strains I-4538, I-4749 and I-4829 are comparable. In contrast, for strain I-4953, it is notable that $CO_2$ production (and consequently ethanol production) is faster and greater than that observed for the 3 other strains.

These results confirm that a strain more resistant to acetic acid during xylose fermentation was obtained and that it is therefore globally more effective.

III) Conclusions:

With the method described, it was therefore possible to select at least one stable strain, I-4953, which retained its capability for fermenting glucose with a limited initiation delay, while showing improved xylose fermentation kinetics in the presence of acetic acid.

The invention claimed is:

1. A yeast strain characterized in that it was deposited at the CNCM (Collection Nationale de Cultures de Microorganismes, Institut Pasteur, 25 rue du Docteur Roux, 75724 Paris Cedex 15) under number 1-4953 on Jan. 29, 2015.

2. A yeast obtained by culturing the strain according to claim 1.

3. The yeast strain according to claim 1, further comprising one or more genetic modifications which do not negatively impact xylose metabolism in the presence of acetic acid.

4. A method for producing fermentation products or ethanol comprising the following steps:
   Incubation of a material or medium containing xylose with the yeast strain according to claim 1;
   Fermentation under anaerobic or semi-anaerobic conditions; and
   Recovery of the one or more fermentation products, or ethanol.

5. The method according to claim 4, characterized in that the material or medium also contains glucose.

6. The yeast strain of claim 1, further comprising at least one copy of an exogenous gene encoding xylose isomerase.

7. The yeast strain according to claim 1, further comprising at least one supernumerary copy of a GAL2 gene.

8. The yeast strain of claim 1, further comprising a modification which suppresses aldose reductase activity.

9. The yeast strain according to claim 1, further comprising at least one supernumerary copy of a xylulokinase (XKS1) gene or a modification of a promoter resulting in overproduction of xylulokinase.

10. The yeast strain according to claim 1, further comprising at least one supernumerary copy of a gene in the pentose phosphate pathway or a modification of a promoter resulting in overproduction of a gene product in the pentose phosphate pathway.

11. The yeast strain according to claim 10, wherein the gene of the pentose phosphate pathway is RPE1, RKL1, TKL1, TAL1, or a combination of any of the foregoing.

12. The yeast strain according to claim 1, comprising a modification resulting in the absence of xylose reductase activity in the yeast.

13. The yeast strain according to claim 12, comprising a mutation in a XR or XYL1 gene.

14. The yeast strain according to claim 1, comprising a modification that enables the yeast to ferment arabinose.

\* \* \* \* \*